United States Patent [19]

Stetler-Stevenson et al.

[11] Patent Number: 5,595,885
[45] Date of Patent: Jan. 21, 1997

[54] MATRIX METALLOPROTEINASE INHIBITOR PEPTIDES

[75] Inventors: William G. Stetler-Stevenson, Gaithersburg; Lance A. Liotta, Potomac; Henry C. Krutzsch, Bethesda, all of Md.

[73] Assignee: The United States of America as represented by the Department of Health and Human Services, Washington, D.C.

[21] Appl. No.: 39,525

[22] Filed: Mar. 29, 1993

Related U.S. Application Data

[63] Continuation of Ser. No. 494,796, Mar. 13, 1990, abandoned, which is a continuation-in-part of Ser. No. 395,453, Aug. 18, 1989, abandoned, which is a continuation-in-part of Ser. No. 380,431, Jul. 17, 1989, which is a continuation-in-part of Ser. No. 326,334, Mar. 21, 1989, abandoned.

[51] Int. Cl.$^6$ .................................................. C12N 15/00
[52] U.S. Cl. .................. 435/69.2; 435/172.3; 435/252.3; 536/23.1; 536/23.5; 536/25.3
[58] Field of Search .......................... 435/6, 69.2, 172.3, 435/320.1, 252.3, 240.1; 536/23.1, 23.5, 25.3

[56] References Cited

PUBLICATIONS

Docherty et al "Sequence of human tissue inhibitor of metalloproteinases" Nature vol. 318, pp. 66–69. 7 Nov. 1985.

*Primary Examiner*—Christine M. Nucker
*Assistant Examiner*—Laurie Scheiner
*Attorney, Agent, or Firm*—Townsend and Townsend and Crew

[57] ABSTRACT

The present invention is an isolated protein of 21,600 Da which binds to both latent and activated type IV collagenase with high affinity at 1:1 molar stoichiometry, thereby abolishing enzyme activity. The protein is purified by affinity chromatography on solid phase metalloproteinase, or solid phase metalloproteinase substrates which bind the enzyme-inhibitor complex. The complete primary structure of this protein (initially called CSC-21K), as determined by sequencing overlapping peptides spanning the entire protein, reveals homology with a protein called TIMP, Tissue Inhibitor of Metalloproteinases. In addition, a cDNA for this novel inhibitor, now designated TIMP-2, was cloned from a melanoma cell and its sequence was compared with that of human TIMP-1. Northern blots of melanoma cell mRNA showed two distinct transcripts of 0.9 kb and 3.5 kb which are down-regulated by transforming growth factor-β, and are unchanged by phorbol ester treatment. The inhibitor of the present invention may be used for treatment of pathologic conditions resulting from inappropriate degradation of extracellular matrix molecules by matrix metalloproteinases, such as metastatic neoplasia, myocardial infarction, and arthritis. Therapeutic treatments using this inhibitor may include formulations for inhalation and inclusion complexes adapted for buccal or sublingual administration, or administration of a recombinant DNA molecule which expresses a DNA segment that encodes the matrix metalloproteinase inhibitor of this invention.

7 Claims, 13 Drawing Sheets

| SEQUENCE | | # OF NEW RESIDUES |
|---|---|---|
| #1 | CSCSPVHPQQRFCNADVVIRAKAVSEKEVDSGNDIYGNPI | 40 |
| #2 | DIYGNPIKRIQVEIKQIKKFKGIEK | |
| #3 | GIEKDIEFIY | |
| #4 | DIEFIYTAPSSAVCGVELDUGGK | 41 |
| #5 | DUGGKKEVLIAGKAE | |
| #6 | EDGKRHI | |
| #7 | DGKRHITL | 18 |
| #8 | RHITLCDFIVPWDTLSTTQKK | |
| #9 | DTLSTTQKKSLN | 19 |
| #10 | SLNHRVQQGCECK | |
| #11 | VQQGCEKITR | |
| #12 | ITRCPMIPCYISSPDECLWTDWVTEK | 36 |
| #13 | DWVTEKNINGHQAKFFACIKRS | 16 |
| #14 | RSDGSCAWYRGAAPPK | |
| #15 | GAAPPKQEFLDI | |
| #16 | QEFLDIED | 22 |
| | | 192 |

| SEQUENCE # | DERIVED FROM |
|---|---|
| 1 | N-TERMINAL RUN |
| 2,5,6,7,9,13 | Asp-N DIGESTION PEPTIDES |
| 3,11,15 | Arg-C DIGESTION PEPTIDES |
| 4,8,10,12,14,16 | Lys-C DIGESTION PEPTIDES |

FIG. 4.

```
CSC21K  CSCSPVHPQQAFCNADVVIRAKAVSEKEVDSGNDIYGNPIKRIQYEIKQIKKFKGIE---
                  10        20        30        40        50
        X.|   |||  |||.|. ||||  |.. ...|    .| .|..|. ||..
        | || ||| ||||| |||||.|| |||. | |    .||| .|. .||..
TIMP    CTCVPPHPQTAFCNSDLVIRAKFVGTPEVN-QTTLYQ-----RYEIKMTKMYKGFQALG
                  30        40        50        60        70

CSC21K  --KDIEFIYTAPSSAVCG-VELDVGGKKEYLIAGKAEDGKRHITLCDFIVPWDTLSTTQK
                  70        80        90       100       110
          ||||||||.|..|| ||.|   |.     .|    ||||.|     |.|.||.
        |||||||||| ||| ||  .| ||. .|||.   .| | |.|||  | |||.||||
TIMP    DAADIRFVYTPAMESVCGYFHRSHNRSEEFLIAGKLQDGLLHITTCSFVAPWNSLAQR
                  80        90       100       110       120       130

CSC21K  KSLNHRYQQGC-ECKITRCPMIPCYISSPDECLWTDWVTEKNINGHQAKFFACIKRSDGS
                 120       130       140       150       160       170
        ||  | |||| ||| | |   ||| .||  .||||.|| ||.|||  ||  ||||.|||
        ||v^|..  | |||.|.|   ||| .|| ||||||.||.|| |||  |||.|||| |||
TIMP    RGFTKTYTVGCEECTVFPCLSIPCKLQSGTHCLWTDQLLQGSEKGFQSRHLACLPREPGL
                 140       150       160       170       180       190

CSC21K  CAWYRGAAPPKQEFLDIED
                 180
        | |
        |.|
TIMP    CTWQSLRSQIA
                 200
```

FIG. 5.

```
CCTCCTTGCCTTTCGAAGCATCTTTGGGCAAACTTCTTTCTCAGGCGCTTGATCTTCAGCTCTGCGAAATTCCTTCGCTTTTCTT    87

AAGGGTTTCTNGCACAGCAGGAACCTCCTTCTTCTTCTTCTTCTACACCCTCCGGGAGCAGCTGCAACAGGCGTTTTGCAATGCAGA   174
                                                           Q  Q  A  F  C  N  A  D

TGTAGTGATCAGGGCCAAAGCGGTCAGTGAGAAGGAAGTGGACTCTGGAAACGACATTTATGCAACCCTATCAAGAGGATCCAGTA   261
 V  V  I  R  A  K  A  V  S  N  K  E  V  D  S  G  N  D  I  Y  G  N  P  I  K  R  I  Q  Y

TGAGATCAAGCAGATAAAGATGTTCAAAGGGCCTGAGAAGGATATAGAGTTTATCTACACGGCCCCTCCTCGGCAGTGTGTGGGGT   348
 E  I  K  Q  I  K  M  F  K  G  P  E  K  D  I  E  F  F  I  Y  T  A  P  S  S  A  V  C  G  V

CTCGCTGGACGTTGGCGGAAAGAAGGAATATCTCATTGCAGGAAAGGCCGAGGGGGACGGCAAGATGCACATCACCCTCTGTGACTT   435
 S  L  D  V  G  G  K  K  E  Y  L  I  A  G  K  A  E  G  D  G  K  M  H  I  T  L  C  D  F

CATCGTGCCCTGGGACACCCTGAGCACCACCCAGAAGAAGAGCCTGAACCACAGGTACCAGATGGGCTGCGAGTGCAAGATCACGCG   522
 I  V  P  W  D  T  L  S  T  T  Q  K  K  S  L  N  H  R  Y  Q  M  G  C  E  C  K  I  T  R

CTGCCCCATGATCCCGTGCTACATCTCCTCCCCGGACGAGTGCCTCTGGATGGACTGGGTCACAGAGAAGAACATCAACGGGCACCA   609
 C  P  M  I  P  C  Y  I  S  S  P  D  E  C  L  W  M  D  W  V  T  E  K  N  I  N  G  H . Q

GGCCAAGTTCTTCGCCTGCATCAAGAGAAGTGACGGCTCCTGTGCGTGGTACCGCGGCGCCCCCAAGCAGGAGTTTCTCGA   696
 A  K  F  F  A  C  I  K  R  S  D  G  S  C  A  W  Y  R  G  A  A  P  P  K  Q  E  F  L  D

CATCGAGGACCCCATAAGCAGGCCTCCCAACGCCCCTGTGCCAACTGCAAAAAAGCCTCCAAGGGTTTCGACGGTCCAGCTCTGACA   783
 I  E  D  P

TCCTTCCTGGAAACAGCATGAATAAACACTCATCCCATGGGTCCAAATTAATATGA   841
```

FIG. 6A.

```
CGAGACGCCATGCCCGGGGGCTGGGATCACCATGCCCCTTGCCCGTCTCGCTGTCTGTAACCCCCAGCACCTCCCGC      87

AGGCCTGGACGTCTTATCCCTCTCCTTAGCCCCAGGAGCGTGTTTCATTAACTCTCCTCACCTCTGTCTTGTGTTTTGCAGTGAT   174
                                                                          V  I

CAGGGCCAAAGCGGTCAGTGAGAAGGAAGTGGACTCTGGAAACGACATTTATGGCAACCCTATCAAGAGGATCCAGTATGAGATCAA   261
 R   A   K   A   V   S   E   K   E   V   D   S   G   N   D   I   Y   G   N   P   I   K   R   I   Q   Y   E   I   K

GCAGATAAAGATGTTCAAAGGGCCTGAGAAGGATATAGAGTTTATCTACACGGCCCCTCCTCGGCAGTGTGGGGTCTCGCTGGA     348
 Q   I   K   M   F   K   G   P   E   K   D   I   E   F   I   Y   T   A   P   S   S   A   V   C   G   V   S   L   D

CGTTGGAGGAAAGAAGGAATATCTCATTGCAGGAAAAGCCGAGGGGGACGGCAAGATGCACATCACCCTCTGTGACTTCATCGTGCC    435
 V   G   G   K   K   E   Y   L   I   A   G   K   A   E   G   D   G   K   M   H   I   T   L   C   D   F   I   V   P

CTGGGACACCCTGAGCACCACCCAGAAGAAGAGCCTGAACCACAGGTACCAGATGGGCTGCGAGTGCAAGATCACGCGCTGCCCCAT    522
 W   D   T   L   S   T   T   Q   K   K   S   L   N   H   R   Y   Q   M   G   C   E   C   K   I   T   R   C   P   M

GATCCCGTGCTACATCTCCTCCCCGGACGAGTGCCTCTGGATGGACTGGGTCACAGAGAAGAACATCAACGGGCACCAGGCCAAGTT   609
 I   P   C   Y   I   S   S   P   D   E   C   L   W   M   D   W   V   T   E   K   N   I   N   G   H   Q   A   K   F

CTTCGCCTGCATCAAGAGAAGTGACGGCTCCTGTGCCTGGTACCGCGGGGCGGCCCCCAAGCAGGAGTTTCTGGACATCGAGGA     696
 F   A   C   I   K   R   S   D   G   S   C   A   W   Y   R   G   A   A   P   P   K   Q   E   F   L   D   I   E   D

CCCATAAGCAGGCCTCCAACGCCCCTGTGGCCAACTGCAAAAAAAGCCTCCAAGGGTTTCGACGTCCAGCTCTGACATCCCTTCCT    783
 P

GGAAACAGCATGAATAAAACACTCATCCCATGGGTCCAAATTAATATGA                                     832
```

FIG. 6B.

```
CGGCCCGGCCGACGCCTGCAGCTGCTCCCCGGTGCACCCGCAACAGGCCGTTTTGCAATGCAGATGTAGTGATCAGGGCCAAAGCGG   87
               C   S   C   S   P   V   H   P   Q   Q   A   F   C   N   A   D   V   V   I   R   A   K   A

TCAGTGAGAAGGAAGTGGACTCTGGAAACGACATTTATGGCAACCCTATCAAGAGGATCCAGTATGAGATCAAGCAGATAAAGATGT  174
 V   S   E   K   E   V   D   S   G   N   D   I   Y   G   N   P   I   K   R   I   Q   Y   E   I   K   Q   I   K   M

TCAAAGGGCCTGAGAAGGATATAGAGTTTATCTACACGGCCCCCTCCTCGGCAGTGTGTGGGGTCTCGCTGGACGTTGGAGGAAAGA  261
 F   K   G   P   E   L   D   I   E   F   I   Y   T   A   P   S   S   A   V   C   G   V   S   L   D   V   G   G   K

AGGAATATCTCATTGCAGGAAAAGCCGAGGGGACGGCAAGATGCACATCACCCTCTGTGACTTCATCGTGCCCTGGGACACCCTGA   348
 K   E   Y   L   I   A   G   K   A   E   G   D   G   K   M   H   I   T   L   C   D   F   I   V   P   W   D   T   L

GCACCACCCAGAAGAAGAGCCTGAACCACAGTTACCAGATGGGCTGCGAGTGCAAGATCACGCGCTGCCCCATGATCCCGTGCTACA  435
 S   T   T   Q   K   K   S   L   N   H   R   Y   Q   M   G   C   E   C   K   I   T   R   C   P   M   I   P   C   Y

TCTCCTCCCCGGACGAGTGCCTCTGGATGGACTGGGTCACAGAGAAGAACATCAACGGGCACCAGGCCAAGTTCTTCGCCTGCATCA  522
 I   S   S   P   D   E   C   L   W   M   D   W   V   T   E   K   N   I   N   G   H   Q   A   K   F   F   A   C   I

AGAGAAGTGACTGCTCCTGTGCCGTGGTACCGCGGGGCGGCGCCCCCAAGCAGGAGTTTCTGACATCGAGGACCCATAAGCAGGCC  609
 K   R   S   D   C   S   C   A   W   Y   R   G   A   A   P   P   K   Q   E   F   L   D   I   E   D   P

TCCAACGCCCCTGTGGCCAACTGCAAATGCAAAAAAGCCTCCAAGGGGTTTGCGACGGTTCCAGCTCTGACATCCCTTCCTGAAACAGCATGAA  696

TAAAAACACTTCATCCCATGGGGTCCAAATTAATATG  730
```

FIG. 7.

```
CSCSTVHPQQ  AFCNADVVIR  AKAVSEKEVD  SGNDIYGNPI  KRIQYEIKQI  KKFKGIEKDI  EFIYTAPSSA   CSC 21K
     *                                                           *
CSCSPVHPQQ  AFCNADVVIR  AKAVSEKEVD  SGNDIYGNPI  KRIQYEIKQI  KMFKGPEKDI  EFIYTAPSSA   TIMP 2

VCGVELDVGG  KKEYLIAGKA  E DGKRHITL  CDFIVPWDTL  STTQKKSLNH  RYQQGCECKI  TRCPMIPCYI   CSC 21K
     *                       *                                   *
VCGCSLDVGG  KKEYLIAGKA  EGDGKMHITL  CDFIVPWDTL  STTQKKSLNH  RYQMGCECKI  TRCPMIPCYI   TIMP 2

SSPDECLWTD  WVTEKNINGH  QAKFFACIKR  SDGSCAWYRG  AAPPKQEFLD  IED                      CSC 21K
     *                                                        *
SSPDECLWMD  WVTEKNINGH  QAKFFACIKR  SDGSCAWYRG  AAPPKQEFLD  IEDP                     TIMP 2
```

FIG. 8.

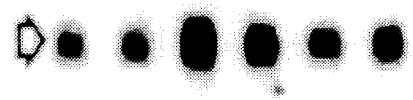
FIG. 12.

MATRIX METALLOPROTEINASE INHIBITOR PEPTIDES

This application is a continuation of application Ser. No. 07/494,796, filed Mar. 13, 1990, now abandoned, which is a continuation-in-part of application Ser. No. 07/395,453, filed Aug. 18, 1989, now abandoned, which is a continuation-in-part of application Ser. No. 07/380,431, filed Jul. 17, 1989, which is a continuation-in-part of application Ser. No. 07/326,334, filed Mar. 21, 1989, now abandoned.

BACKGROUND OF THE INVENTION

1. Field of the Invention

This invention relates to isolated proteins or peptides useful for inhibition of matrix metalloproteinases. Specifically, this invention relates to a novel protein, isolated from conditioned media of cultured human tumor cells, which binds with high affinity to matrix metalloproteinase enzymes and analogs thereof. The natural protein is defined by a novel amino acid sequence including specific positions of cysteine residues. This invention further relates to a novel means of purifying matrix metalloproteinase inhibitors using metalloproteinase affinity chromatography.

2. Background

The collagenase family of enzymes are a group of neutral metalloproteinases, also known as matrix matalloproteinases, which are secreted in the zymogen form and degrade both the collagenous and noncollagenous components of the extracellular matrix. All require a metal ion (calcium and/or zinc) for hydrolytic activity, and all are secreted in the latent pre-enzyme form. Members of this collagenase gene family include: the interstitial collagenases, which degrade collagen types I, II and III and have been characterized with respect to substrate specificity and requirements for activation (Stricklin, G. P., Jeffrey, J. J., Rosewit, W. T., and Eisen, A. Z., 1983, *Biochemistry* 22, 61–68; Goldberg, G. I., Wilhelm, S., Kronberger, A., Bauer, E. A., Grant, G. A., and Eisen, A. Z., 1986, *J. Biol. Chem.* 261, 6600–6605; Hasty, K. A., Jeffrey, J. J., Hibbs, M. S., and Welgus, H. G., 1987, *J. Biol. Chem.* 262, 10048–1052; Fields, G. B., Van Wart, H. E., and Birkedal-Hansen, H., 1987, *J. Biol. Chem.* 262, 6221–6226; Grant, G. A., Eisen, A. Z., Marmer, B. L. Rosweit, W. T., and Goldberg, G. I., 1987, *J. Biol. Chem.* 262, 5886–5889); stromelysin, which degrades proteoglycans, glycoproteins, and the non-helical portions of collagenous molecules (Wilhelm, S. M., Collierm, I. E., Kronberger, A., Eisen, A. Z., Marmer, B. L., Grant, G. A., Bauer, E., and Goldberg, G. I., 1987, *Proc. Natl. Acad. Sci. U.S.A.* 84, 6725–6729; Whitman, S. E., Murphy, G., Angel, P., Rahmsforf, H. J., SMith, B. J., Lyons, A., Harris, T. J. T., Reynolds. J. J., Herrlich, P. and Docherty, A. J. P., 1986, *Biochem. J.* 240, 913–916); and type IV collagenase, which degrades pepsin-resistant triple-helical type IV collagen and interstitial collagens (gelatin). Type IV collagenase has been identified in human tumor cells (Liotta, L. A., Kleinerman, J, Catanzaro, P., and Rynbrandt, D., 1977, *J. Natl. Cancer Inst.* 58, 1427–1439; Turpeenniemi-Hujanen T., and Tryggvason, K., 1982, *Int. J. Cancer* 30p, 669–673; Liotta, L. A., Abe, S., Gehron-Robey, P., and Martin, G. R., 1979, *Proc. Natl. Acad. Sci. U.S.A.* 76 268–2272; Liotta, L. A., Tryggvasson, K., Garbisa, S., Hart, I., Foltz, C. M., and Shafie, S., 1980, *Nature* (London) 284, 67–68; Collier, I. E., Wilhelm, S. M., Eisen, A. Z., Mariner, B. L., Grant, G. A., Seltzer, J. L., Kronberger, A., He., C., Bauer, E. A., and Goldberg, G. I., 1988, *J. Biol. Chem.* 263, 6579–6587), endothelial cells (Kalebic, T., Barbisa, S., Glaser, B., and Liotta, L. A., 1983, *Science* 221, 281–283), bone (Murphy, G., McAlpine, C. G., Poll, C. T., and Reynolds, J. J., 1985, *Biochem. Biophys. Acta* 831, 49–58), fibroblasts (Collier, I. E., Wilhelm, S. M., Eisen, A. Z., Marmer, B. L., Grant, G. A., Seltzer, J. L., Kronberger, A., He., C., Bauer, E. A., and Goldberg, G. I., 1988, *J. Biol. Chem.* 263, 6579–6587), polymorphonuclear leukocytes (Uitto, V. J., Schwartz D., and Veis, A., 1980, *Eur. J. Biochem.* 105, 409–417) and macrophages (Garbidsa, S., Ballin, M., Daga-Giordini, D., Fastelli, G., Naturale, M., Negro, A., Semenzato, G., and Liotta, L. A., 1986, *J. Biol. Chem.* 261, 2369–2375). This enzyme is a neutral metalloproteinase of 68 to 72 kilodaltons which is secreted in zymogen form (Liotta, L. A., Abe, S., Gehron-Robey, P., and Martin, G. R., 1979, *Proc. Natl. Acad. Sci. U.S.A.* 76, 2268–2272; Liotta, L. A., Tryggvassin, K., Garbisa, S., Gehron-Robey, P., and Abe, S., 1981, *Biochemistry* 20, 100–104; Salo, T., Liotta, L. A., and Tryggvsasson, K., 1983, *J. Biol. Chem.* 258, 3058–3063). In addition, several other members of this collagenase gene family have been described recently, including a second type of stromelysin (stromelysin-2), a 92 kilodalton form of type IV collagenase, and Putative Uterine Metalloproteinase (PUMP)-1, a low molecular weight uterine collagenase (Wilhelm, S. M., Collier, I. E., Marmer, B. L., Eisen, A. Z., Grant, G. A., and Goldberg, G. I., 1989, *J. Biol. Chem.* 264, 17213–17221; Woessner, J. F. and Talpin, C. J., 1988, *J. Biol. Chem.* 263, 16918–16925).

The matrix metalloproteinases are thought to play an important role in disease processes characterized by the inappropriate destruction of the extracellular matrix. The diseases include inflammatory processes such as rheumatoid arthritis and other autoimmune disorders, tumor cell invasion and metastasis formation, local sequelae of myocardial anoxia, and corneal ulceration (Okada et al., 1986, *J. Biol. Chem.* 261, 14245–14255; Harris et al., 1984, *Collagen Relat.* 4, 493–512; Werb et al., 1977, *New Engl. J. Med.* 296, 1017–1023; Liotta et al., 1980, *Nature (London)* 284, 67–68; Kalebic et al., 1983, *Science* 221, 281–283). Many tissues contain natural inhibitors of the matrix metalloproteinases. In some cases, this inhibitory activity is derived from the antiproteases in plasma, particularly $\alpha_2$-macroglobulin and $\beta_1$-anticollagenase. $\alpha_2$-Macroglobulin is a high molecular weight (725,000 Da) inhibitor present in serum. It is thought to account for 95% of the collagenolytic inhibitory activity present in serum. Because of its large size, it is normally unable to pass the vascular permeability barrier. Under conditions of extreme inflammation in which there is increased capillary permeability, $\alpha_2$-macroglobulin may enter the tissue compartments and play a role in the regulation of matrix metalloproteinases. The mechanism of inhibition of the matrix metalloproteinases by $\alpha_2$-macroglobulin has not been directly studied. However, it is thought to be similar to the mechanism whereby $\alpha_2$-macroglobulin causes inhibition of other proteases. Hence, the mechanism is not believed to be unique for the matrix metalloproteinases.

$\beta_1$-Anticollagenase is approximately 40,000 daltons in size. It accounts for approximately 5% of the metalloproteinase inhibiting activity of serum. This inhibitor is thought to pass the vascular permeability barrier and be widely distributed in the tissue compartments. $\beta_1$-Anticollagenase may be related to another group of natural inhibitors of the metalloproteinases referred to as TIMPs, tissue inhibitors of metalloproteinases. The down-regulation of metalloproteinase collagenolysis and proteolysis may occur through TIMPs.

The prototype TIMP, TIMP-1, is a glycoprotein with an apparent molecular size of 28.5 kDa which forms a complex of 1:1 stoichiometry with activated interstitial collagenase, stromelysin, and the 92 kDa type IV collagenase (Welgus and Stricklin, 1983, *J. Biol. Chem.* 253, 12259–12264: Welgus et al., 1985a, *Collagen Rel. Res.* 5, 167–179; Wilhelm et al., 1989, *J. Biol. Chem.* 264, 17213–17221; European patent 189,784). The gene coding for TIMP-1 has been cloned, sequenced and mapped to the X-chromosome (Carmichael et al., 1986, *Proc. Natl. Sci. USA* 83, 2407–2411; Docherty et al., 1985, *Nature (London)* 318, 66–69; Mullins et al., 1988, *Genomics* 3, 187–194; Mahtani et al., 1988, Genomics 2, 294–301). The secreted protein has 184 amino acids and six intramolecular disulfide bonds. Reduction and alkylation of TIMP-1 abolishes all inhibitory activity. The same cells which produce interstitial collagenase are capable of synthesizing and secreting TIMP-1 (Welgus et al., 1985b, *J. Clin. Invest.* 76, 219–224; Herron et al., 1986, *J. Biol. Chem.* 261, 2814–2818). Thus, the net collagenolytic activity for these cell types is the result of the balance between activated enzyme levels and TIMP-1 levels. Studies have shown an inverse correlation between TIMP-1 levels and the invasive potential of murine and human tumor cells. Downmodulation of TIMP-1 mRNA levels by use of TIMP-1 antisense RNA resulted in conversion of previously nontumorigenic, noninvasive Swiss 3T3 cells to tumorigenic cells with invasive properties in vitro and metastatic potential in vivo (Khokha et al., 1989, *Science* 243, 947–950).

Another class of biologically active collagenase inhibitors is composed of low molecular weight (>10,000 daltons) cationic proteins isolated from cartilage, aorta and teeth, but which are poorly characterized.

Recently several new members of the matrix metalloproteinase family have been identified, with various substrate specificities. These include stromelysin (homologue of rat transin), type IV collagenase (70 kDa gelatinase) and a 92 kDa gelatinase. While also identified in normal cell types, the over-expression of these enzymes has been linked to malignant conversion and the metastatic phenotype in a number of systems. Thus, there is a need to understand the molecular basis of the regulation of these metalloproteinases and to find inhibitors which can be exploited for diagnostic and therapeutic purposes.

SUMMARY OF THE INVENTION

It is the object of this invention to provide means of purifying natural inhibitors of metalloproteinases.

It is a further object of this invention to provide matrix metalloproteinase inhibitors and derivatives thereof. The inhibitors may be obtained from natural sources, may be produced by synthetic means such as the Merrifield peptide synthesis process, or by genetically engineered organisms or cell lines. The inhibitors of the invention may be used to treat disease conditions which result from activity of matrix metalloproteinases. Furthermore, since metalloproteinase activity is essential to the implantation of the zygote, these inhibitors are useful as contraceptives.

The present invention relates to novel metalloproteinase inhibitors distinct from previous inhibitors mentioned above. Described herein are the isolation and sequencing of a novel protein, now designated TIMP-2 (initially called CSC-21K, so named for its amino terminal amino acid sequence and apparent molecular weight on gel electrophoresis). CSC-21K forms a 1:1 complex with type IV procollagenase and type IV collagenase and inhibits activated type IV collagenase. Binding of CSC-21K to activated type IV collagenase results in inhibition of its collagenolytic activity. This inhibitor can be isolated using affinity chromatography on purified matrix metalloproteinase attached to a solid phase. Amino acid sequence analysis of CSC-21K reveals significant homology to TIMP-1 indicating that CSC-21K is the first novel additional member of the family of TIMP-like proteins.

Thus, a preferred embodiment is a protein of approximately 21,600 daltons which binds to matrix metalloproteinases and can be isolated using affinity chromatography on solid phase purified metalloproteinases. The amino acid sequence of this isolated protein shows that it is a new gene product not previously discovered and has areas of sequence homology with the known natural tissue inhibitor of metalloproteinases (TIMP-1). The protein of the preferred embodiment of this inhibitor is characterized by the amino acid sequence shown in FIG. 5, below.

DESCRIPTION OF THE FIGURES

FIG. 4. CSC-21K protein sequence data obtained from the amino terminus and following digestions with endoproteinases Lys-C, Arg-C and Asp-N. Peptide sequences obtained following digests were aligned by overlaps (underlined regions) as shown. The entire sequence of CSC-21K is encompassed by these overlapping peptides. The origin of each of the peptides is identified in the lower half of the figure.

FIG. 5. Complete sequence for CSC-21K (TIMP-2) derived from direct amino acid sequencing and homology to human TIMP-1. Computerized homology searches using the BIONET system were applied to the sequence obtained following digestions with endoproteinases Lys-C, Arg-C and Asp-N. The results of these homology searches are shown.

FIG. 6. cDNA sequence and deduced protein sequence of clones pSS15 and pSS18 which encode portions of CSC-21K.

FIG. 7. Nucleotide sequence and prediction amino acid sequence of a complete human TIMP-2 cDNA. The cDNA insert of clone pSS38 was sequenced in both directions using dideoxy-methodology. The predicted amino acid sequence is shown under the DNA sequence. The putative polyadenylation signal is underlined.

FIG. 8. Comparison of TIMP-2 deduced amino acid sequence and direct amino acid sequencing of CSC-21K protein (see FIG. 5, above). CSC-21K primary structure was determined directly using a Porton Instruments 2020 gas phase protein sequenator and phenyl hydantoin derivative identification on a Beckman System Gold HPLC unit equipped with a 0.46×25 cm Beckman ODS column. Comparison shows 96% identity of these sequences. Asterisks identify changes in the sequence identified by DNA sequencing of the complete TIMP-2 cDNA.

FIG. 12. Northern blot analysis of human colorectal tumors and adjacent normal mucosa. RNA (5 µg) of each sample was electrophoresed and transferred as described in the text. Lanes $T_1$, $T_2$ and $T_3$ contain RNA from the invasive colorectal tumors. Lanes $N_1$, $N_2$ and $N_3$ contain RNA from the corresponding adjacent normal mucosa.

DETAILED DESCRIPTION OF THE INVENTION

Figure 1:
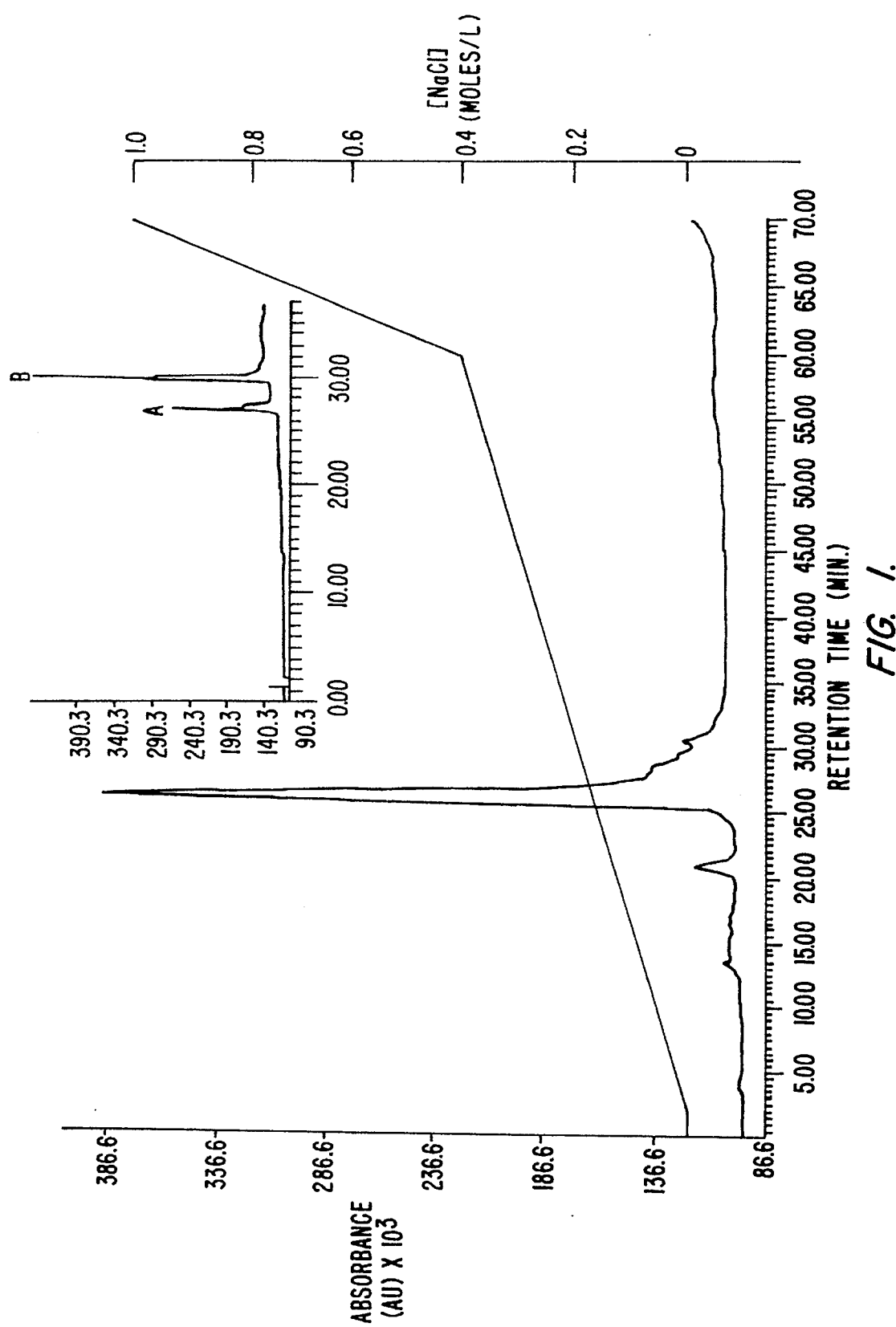
FIG. 1. Anion exchange chromatography of the complex of collagenase type IV and inhibitor isolated from human melanoma cell (A2058) conditioned media and eluted from gelatin affinity chromatography. 15 µg of gelatin-affinity purified material were applied to the anion exchange resin. The column was eluted with a linear gradient of NaCl (--). Material from the single major peak eluting at 0.18 M NaCl was rechromatographed on the reverse phase column (insert). Material from peaks A and B were sequenced directly (see FIG. 2B).

The present invention relates to an inhibitor of matrix metalloproteinases for which the determination of the complete primary structure shows that this protein is a second member of the TIMP family, TIMP-2, as recently reported (Stetler-Stevenson et al., 1989, J. Biol. Chem. 264, 17374–17378). TIMP-2 is a 21 kDa protein which selectively forms a complex with the latent proenzyme form of the 72 kDa type IV collagenase (Stetler-Stevenson et al., 1989, J. Biol. Chem. 264, 17374–17378, Goldberg et al., 1989, Proc. Natl. Acad. Sci. USA 86, 8207–8211). The secreted protein has 192 amino acid residues and is not glycosylated. TIMP-2 shows an overall 71% homology to TIMP-1 at the amino acid sequence level. The position of the twelve cysteine residues are conserved with respect to those present in TIMP-1, as are three of the four tryptophan residues. TIMP-2 inhibits the type IV collagenolytic activity and the gelatinolytic activity associated with the 72 kDa enzyme. Inhibition studies demonstrated that complete enzyme inhibition occurred at 1:1 molar ratio of TIMP-2 to activated 72 kDa type IV collagenase enzyme (Stetler-Stevenson et al., 1989, J. Biol. Chem. 264, 17374–17378). Thus unlike TIMP-1, TIMP-2 is capable of binding to both the latent and activated forms of type IV collagenase. Cell culture studies using cell lines that produce a variety of collagenase family enzymes, as well as both TIMP-1 and TIMP-2, suggest that TIMP-2 preferentially interacts with the 72 kDa type IV collagenase (Stetler-Stevenson et al., 1989, J. Biol. Chem. 264, 17374–17378; Goldberg et al., 1989, Proc. Natl. Acad. Sci. USA 86, 8207–8211). Thus, like interstitial collagenase activity which is the balance of activated enzyme and TIMP-1, the net 72 kDa type IV collagenase activity may depend upon the balance between the levels of activated enzyme and TIMP-2.

Analogs of the natural inhibitor of the invention can be made by preparing peptides and proteins having cysteines at the same intervals as the cysteines in the natural inhibitor. Other amino acids may vary from the pattern of the natural inhibitor so long as the cysteine is located at the appropriate intervals. At least two appropriately spaced cysteines must be present in the peptide to ensure inhibitory activity by virtue of a disulfide bridge formation.

While the preferred protein contains the sequence of FIG. 5, peptides having amino acids identical with the sequence of FIG. 5 in at least 50% of the sequence positions are within the scope of the invention having useful inhibitor of metalloproteinase activity provided the cysteines are retained in the desired relative positions.

Peptide fragments derived from the natural CSC-21 molecule were used as immunogens. In the case of synthetic peptide fragments of the protein to be used as immunogens or antigens for antibodies specific for CSC-21K, one skilled in the art understands that a unique amino acid sequence in terms of recognition by an antibody binding site consists of a sequence of from four to six amino acids which is not known to exist in another protein in the environment for which the antibody is to be used (e.g., human biological specimens). Further, a unique nucleotide sequence in this context refers to the nucleotide sequence encoding a unique amino acid sequence as defined above and, therefore, consists of from four to six codons (12 to 18 nucleotides) needed to encode four to six amino acids. Antibodies to such unique protein fragments can be used to detect the natural inhibitor in serum, tissue, and other natural sources.

Particularly preferred peptides are those having at least 2 cysteines. An amino acid sequence containing the sequence CSCSPVHPQQAFCNA derived from the amino terminal of the molecule and segments containing the amino acid sequences SLNHRYQQGCECKITRCP and MIPCYISSP-DECLWTD appear particularly active. The antigenic and functional utility of peptides derived from CSC-21K is not limited to these peptides but can include the whole protein, natural or synthetically derived.

EXAMPLE 1

Purification of CSC-21K (TIMP-2)

Human A2058 melanoma cells were grown to 80% confluence in Dulbecco's modified Eagle's medium with 10% fetal bovine serum. The medium was then replaced with serum-free Dulbecco's modified Eagle's medium, and the culture continued for an additional 24 hours. Approximately 60 L of human melanoma cell (A2058) serum-free conditioned medium was concentrated to 300 mL using an Amicon YM 30 ultrafiltration membrane. This concentrated conditioned medium was applied to two 1.0×10 cm gelatin-Sepharose (Sigma Chemical Co.) affinity columns in series, equilibrated with 0.05 M Tris HCl, 0.5 M NaCl, 0.005 M $CaCl_2$, 0.02% Brij 35, pH 7.6 buffer. The columns were then washed with equilibration buffer before eluting with 10.0% DMSO in equilibration buffer. The eluate was concentrated and exchanges into 0.05 M Tris HCl, 0.15 M NaCl, 0.005 M $CaCl_2$, 0.02% Brij 35, pH 7.6 using as Amicon YM 30 membrane. The samples were stored at −80° C. Samples for anion exchange chromatography were dialyzed into 0.01 M Tris HCl, pH 7.5, with 20% ethylene glycol. A 15 μg sample was injected into a Dionex AI400 HPLC system equipped with a 0.4×5.0 cm Dionex ProPac anion exchange column. This column was eluted with a linear gradient of zero to 0.4 M NaCl. The material under the single major peak was collected and an aliquot was applied to a 0.46×10 cm RP300 column (Pierce Chemical Co.). This column was eluted as previously described (U.S. patent application Ser. No. 07/317,407, filed Mar. 1, 1989, by Liotta et al.). Alternatively, the complex as obtained from gelatin-Sepharose chromatography and stored at −80° C. can be applied directly to the RP300 column system.

Figure 2:
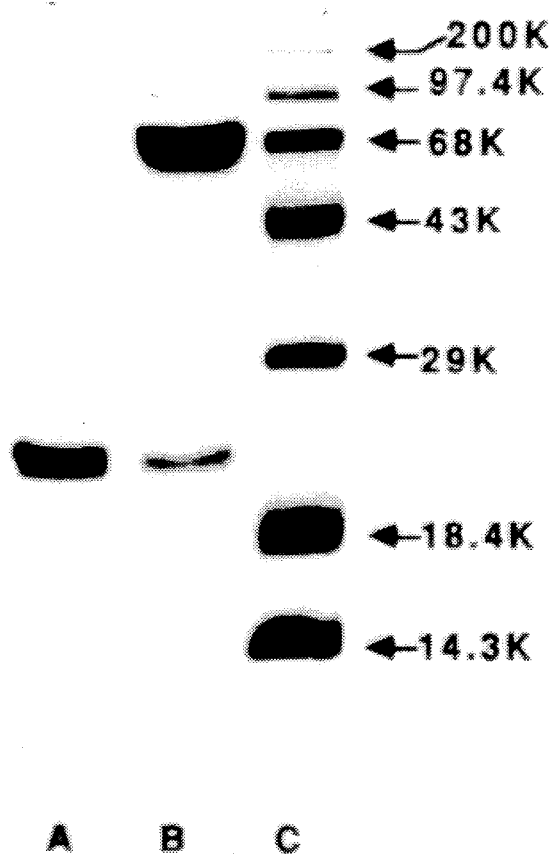
FIG. 2. A. 15% polyacrylamide-SDS gel electrophoresis of CSC-21K and CSC-21K-type IV collagenase complex. Lane A. 2 µg of CSC-21K (peak A) material following reverse phase HPLC purification. Lane B. 2µg of CSC-21K-type IV collagenase complex isolated by gelatin-Sepharose affinity chromatography. Gel was run at 25 milliamps constant current, using a Laemmli sample buffer system and sample buffer containing β-mercaptoethanol. Samples were heated at 95° C. for 2 min prior to electrophoresis. B. Amino terminal amino acid sequence of reverse phase HPLC peaks. The complex obtained following gelatin-affinity and anion exchange chromatography was further purified into components by reverse phase HPLC. The materials obtained in peaks A and B (FIG. 1, insert) were sequenced directly.

CSC-21K was isolated as a complex with human type IV collagenase by gelatin affinity chromatography of human melanoma cell (A2058) conditioned media. Anion exchange chromatography of the material obtained from gelatin-affinity chromatography resulted in a single species eluting at approximately 0.18 M NaCl (FIG. 1). Reverse phase HPLC analysis of material eluted from the ion exchange chromatography showed that this material contained two components (FIG. 1, insert). The material obtained from the gelatin-affinity chromatography step is thus an intermolecular complex as seen on anion exchange chromatography, and is not a simple copurification of two species on gelatin-affinity chromatography. $NaDodSO_4$-PAGE of the complex obtained from the gelatin-affinity chromatography also showed two components, FIG. 2A. The higher molecular weight material has an $M_r$ of 70,000. It was identified as type IV procollagenase by immunoblotting and amino terminal sequencing (vide infra). The lower molecular weight material has an apparent $M_r$ of 18,000 which increased to 21,000 upon reduction. Direct reverse phase HPLC analysis of the complex obtained from gelatin affinity chromatography resulted in the separation of two peaks identical to those in the insert of FIG. 1. The material obtained from each of these peaks, designated peak A for the material with the shorter retention time and peak B for the material of longer retention time, was subjected to amino acid analysis and direct amino acid sequencing. Peak A material gave a unique amino-terminal amino acid sequence shown in FIG. 2B. This material is referred to as CSC-21K. Peak B material gave an amino-terminal sequence identical to latent type IV collagenase (i.e., type IV procollagenase), FIG. 2B.

EXAMPLE 2

Enzyme digestions, amino acid sequencing, and amino acid composition analyses

HPLC purified CSC-21K was reduced and alkylated as described. 15 μg of reduced and alkylated CSC-21K was incubated with 5 μg of endoproteinase Lys-C, 5 μg of endoproteinase Arg-C, or 2 μg of endoproteinase Asp-N in 0.1 M $NH_4HCO_3$ buffer overnight at 37° C. The digests were then separated by reverse phase HPLC on the RP300 column into component peaks which were collected and sequenced individually. Amino acid sequence analysis was carried out on HPLC-purified fractions on a Porton Instruments 2020 Gas Phase Protein Sequenator using standard program 39. PTH amino acid identification was carried out on a Beckman System Gold HPLC unit equipped with a 0.46×25 Beckman ODS column and eluted using a modified sodium acetate/ THF/acetonitrile separation method.

Amino acid composition analyses were performed following vapor phase hydrolysis for 18 h using 6N HCl, 0.1% phenol at 120° C. The hydrolysate was derivatized using the PITC method (PicoTag system, Waters) and analyzed in the same HPLC unit as above using a modified triethylamine/ ammonium acetate/acetonitrile elution method.

Amino acid composition analyses of the complex eluted from the gelatin-affinity chromatography, and CSC-21K are compared in Table 1. The amino acid composition of CSC-21K is significantly different from other collagenase inhibitors and is distinguished by an unusual Leu/Ile ratio. This feature was used to evaluate the stoichiometry of the complex as isolated by gelatin affinity chromatography. Based on the experimentally determined molar amino acid composition of CSC-21 (7 Leu, 18 Ile; Table 1, which is in agreement with the direct amino acid sequence from overlapping peptides, FIG. 4) and the deduced composition of type IV procollagenase (39 Leu/25 Ile), it was calculated that the theoretical Leu/Ile ratio of a 1:1 molar complex would be 46 Leu/42 Ile or 1.10. This is in excellent agreement with the ratio value of 1.03 that was determined from the amino acid composition analysis of the CSC-21K-type IV procollagenase complex. Thus human melanoma cells, which are known to secrete several metalloproteinases, also secrete a protein, CSC21K, which specifically binds to the latent form of type IV collagenase and forms a complex with 1:1 molar stoichiometry.

TABLE 1

Amino acid compositions of CSC-21K
(TIMP-2) and the CSC-21K + Collagenase IV Complex

| AMINO ACID RESIDUE | CSC-21K Picamoles[1] | CSC-21K RESIDUES MOLE[2] | Complex Picamoles[1] |
| --- | --- | --- | --- |
| ASP/ASN | 141 | 18 | 149 |
| GLU/GLN | 166 | 22 | 127 |
| SER | 107 | 14 | 78 |
| HIS | 32 | 4 | 25 |
| GLY | 222 | 29 | 123 |
| ARG | 56 | 7 | 61 |
| THR | 59 | 8 | 86 |
| ALA | 108 | 14 | 92 |
| PRO | 93 | 12 | 92 |
| TYR | 60 | 8 | 64 |
| VAL | 86 | 11 | 67 |
| MET | 11 | 1 | 28 |
| CYS | 33 | 4 | 12 |
| ILE | 137 | 18 | 83 |

TABLE 1-continued

Amino acid compositions of CSC-21K
(TIMP-2) and the CSC-21K + Collagenase IV Complex

| AMINO ACID RESIDUE | CSC-21K Picamoles[1] | CSC-21K RESIDUES MOLE[2] | Complex Picamoles[1] |
| --- | --- | --- | --- |
| LEU | 57 | 7 | 81 |
| PHE | 50 | 7 | 86 |
| LYS | 127 | 17 | 107 |
| TOTAL | 1545 | 201 | 1361 |
| LEU/ILE RATIO | 0.42 | 0.39 | 1.02 |

[1]Data obtained from direct amino acid composition analysis of reduced and alkylated CSC-21K, or enzyme inhibitor complex as isolated by gelatin-Sepharose chromatography, as described above.
[2]Molar amino acid composition calculated from amino acid composition data assuming 7 phenylalanine residues per mole of CSC-21K.

The complete primary structure of human CSC21K, determined by sequence analysis of overlapping peptides obtained following endoproteinase Lys-C, endoproteinase Arg-C and endoproteinase Asp-N digestions, is shown in FIG. 4. The amino acid composition of CSC-21K determined from this sequence data concurs with that obtained by direct analysis of purified CSC21K, Table 1. The molecular weight of CSC-21K calculated from the primary sequence is 21,600 daltons, which is in good agreement with the gel electrophoresis data. Computer searches for homology were performed on the BIONET Protein Data Base (which accesses the NBRF-PIR and SWISS-PROT protein sequence data banks). Computerized homology searches were applied to the entire peptide sequence. This provided the basis for alignment of the CSC-21K structure with that of human TIMP, FIG. 5. CSC-21K shares significant homology with TIMP. There is 41.0% amino acid identify and 29% conservative substitutions in a 191 amino acid overlap. The positions of the twelve cysteine residues are conserved and the positions of three of four tryptophan residues are also conserved. The conservation of the relative positions of these residues supports their functional or structural roles in both proteins.

EXAMPLE 3

Collagenolytic and gelatinolytic inhibition.

Type IV collagenase assays were performed as previously described (U.S. patent application Ser. No. 07/317,407, filed Mar. 1, 1989, by Liotta et al.). Gelatinase assays were performed by adaptation of this method utilizing heat denatured rat skin collagen (NEN/Dupont). The CSC-21-collagenase IV proenzyme complex was activated by a 1 h preincubation with 1 mM p-aminophenylmercuric acetate (p-APMA). Subsequently, purified CSC-21K was added prior to the assay of collagenase IV activity.

Figure 3A:
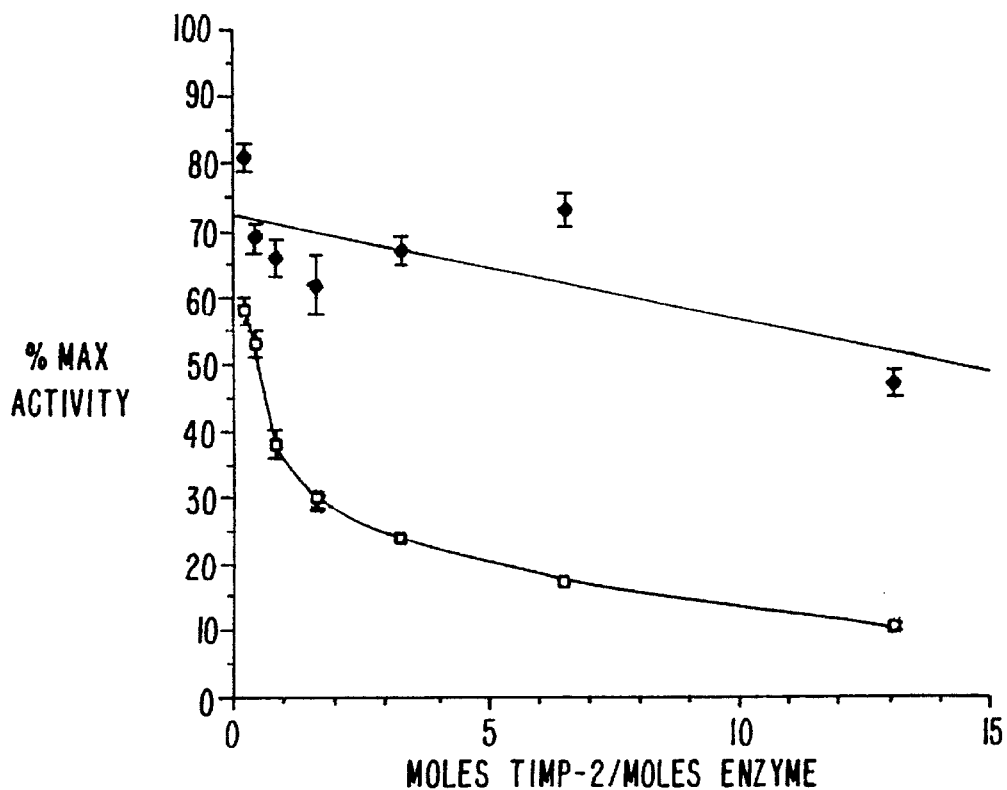
FIGS. 3A and 3B CSC-21K inhibition of activated type IV collagenase/gelatinase activity. 3A. Dose relationship of purified CSC-21 (upper curve with, lower curve without reduction and alkylation) inhibition of purified, p-APMA activated type IV collagenase. CSC-21K is termed TIMP-2 and presented as a mole/mole basis. The substrate is native type IV collagen. 3B. Dose relationship of purified CSC-21K (termed TIMP-2) inhibition of purified p-APMA activated type IV collagenase. The substrate is gelatin.
Figure 3B:
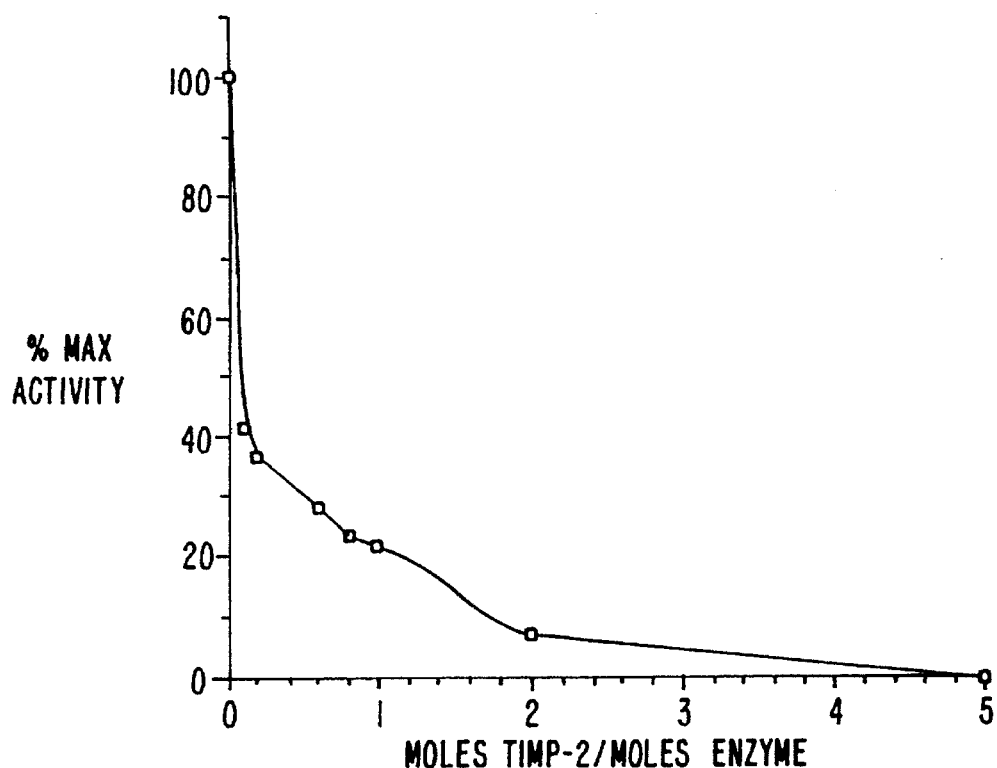

As isolated following gelatin-affinity chromatography, the complex between CSC-21K and type IV procollagenase possessed no collagenolytic activity. Following activation with the organomercurial compound p-amino-phenylmercuric acetate (p-APMA), the maximum achievable type IV collagenolytic activity obtained was 7.12 µg type IV collagen degraded /h/µg enzyme complex. The maximum gelatinolytic activity obtained following organomercurial activation was 26.4 µg/h/µg of enzyme complex. Reduction of disulfide bonds destroys the complex formed between TIMP and interstitial collagenase and also destroys the complex between CSC-21K and type IV procollagenase (FIG. 3A). The addition of purified native CSC21K, but not reduced and alkylated CSC-21K, to this p-APMA activated complex resulted in proportional inhibition of both collagenolytic and gelatinolytic activities (FIG. 3A and B). Extrapolation of this data demonstrated that the binding of CSC-21K to the activated enzyme occurs in a stoichiometric manner that is consistent with the 1:1 molar ratio determined for the complex isolated by gelatin-Sepharose chromatography. These results demonstrate that CSC-21K which has not been exposed to organomercurial compounds is capable of binding to and inhibiting activated type IV collagenase suggest, but they also suggest that p-APMA activation of type IV collagenase may be accompanied by the organomercurial-mediated inactivation of CSC-21K.

These data show that while CSC-21K shares scattered homology with TIMP-1, particularly with respect to conserved positions of the cysteine residues, all of the CSC-21K peptides are distinctly different from sequences of the known TIMP-1. Thus, the peptides of the invention are encoded by a gene different from that which encodes TIMP. This demonstrates that CSC-21K is the product of a separate gene.

Synthetic peptides were prepared using the sequence from the amino terminal portion of the CSC-21K molecule. These were coupled to bovine serum albumin for use in generating anti-peptide antibodies by standard methods. The antibodies were affinity purified using solid phase peptide-affinity chromatography as previously described (Stetler-Stevenson et al., 1989, *J. Biol. Chem.* 264:1353–1356). These antibodies are reactive on standard western and immunoblots.

The isolated, purified CSC-21K, recombinant CSC-21K, and analogs can be used therapeutically in this diseases characterized by the uncontrolled activity of matrix metalloproteinases. Such diseases include arthritis, diabetes, cancer, ulcers of mucosa and epithelial tissues, autoimmune mediated inflammation, lung injury, granulomatous diseases. A particularly useful application may be in the treatment of myocardial infarctions since matrix proteolysis including destruction of the myocardial basement membrane is a harmful process in this affliction. Other therapeutic benefit might also be obtained in diseases with basement membrane destruction such as lupus, autoimmune neural disorders, myocyte destruction such as myodystrophies, myocardial infarct and glomerulopathies. CSC-21K could also be used as a potential birth control agent by preventing embryo/placental attachment or invasion.

EXAMPLE 4 Cloning of Human CSC-21K.

Human A2058 melanoma cells were grown to confluence was run over an oligo dT column to selectively isolate messenger RNA species. This mRNA preparation was then used to prepare a cDNA library using the LambdaGem-4 vector and standard methodology. 1 µg of purified mRNA was used to prepare double stranded cDNA using a commercially available cDNA synthesis kit (Amersham). This cDNA was methylated using EcoRI methylase (Promega), linked to EcoRI linkers (Promega), restricted with EcoRI and ligated to EcoRI digested Lambda-GEM-4 (Promega). The ligations were packaged (Gigapack Gold, Stratagene) and the optimal reactions were pooled to give $1.5 \times 10^6$ recombinants. $7.5 \times 10^5$ recombinants were screened using oligonucleotide 27–40. Oligonucleotide 27–40, a 45–mer, with the sequence: 5'-GAGAAGGAGGTGGACTCTG-GCAATGACATCTATGGCAACAACATC-3', corresponding to the reverse translation of residues 27 through 40 of the previously sequenced TIMP-2 protein. Oligonucleotide 27–40 was synthesized on a Biosearch 8700 DNA synthesizer by means of β-cyanoethyl phosphoramidite chemistry, and was labelled using γ-[$^{32}$P]-ATP (Amersham) and T4 kinase (Bethesda Research Laboratories). From the total of 750,000 plaques screened, 239 positives were identified. Of these positives, initially eight clones were further characterized following SpeI digestion of the parent LambdaGem-4 clones, religation of the SpeI digests and ampicillin resistance selection of the transformants. These eight clones were cross-screened following southern blot hybridization with four additional synthetic oligonucleotides that were also based on the protein sequence data for CSC-21K. Only two clones reacted positively with all four additional synthetic oligonucleotide probes. These clones are designated pSS15 and pSS18. The larger of these two clones is pSS15 which is a pGEM-1 vector containing a 2.1Kb insert. This clone contains an internal HindIII restriction site located approximately 1.2 Kb from the 5' end of the clone. This insert can be released from the pGEM-1 vector by dual endonuclease restriction with EcoRI and XbaI.

Both clones pSS15 and pSS18 were subcloned into M13 and sequenced using the dideoxy method. The pSS15 clone was subcloned using the two HindIII fragments. The partial cDNA sequences obtained and the deduced amino acid sequences are shown in FIG. 6. The amino acid sequence obtained is identical, within the limits of experimental error, to that obtained for a portion of CSC-21K shown in FIG. 5. These results demonstrate that these clones referred to as pSS15 and pSS18 encode the protein CSC-21K. It is obvious that due to differences in codon preferences between species that clones from other species could encode functional CSC-21K protein but with a different nucleotide sequence. Thus, one base change per codon of the CSC-21K cDNA, resulting in 33% change in the overall nucleotide sequence, may still result in a cDNA which would encode a functional CSC-21K protein. Thus, the existence of this clone for human CSC-21K is a reduction to practice of isolating the cDNA encoding this protein from other species.

A deposit of CSC-21K cDNA (pSS15) has been made at the American Type Culture Collection, Rockville, Md. on Aug. 11, 1989 under the accession number 40,644. The deposit shall be viably maintained, replacing if it became nonviable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

In subsequent experiments, two addition clones were isolated and the nucleotide sequence of the cDNA insert in the clone pSS38, the longest, is presented in FIG. 7. The insert contains 730 bp, excluding the poly(AT) tail and encodes the mature TIMP-2 protein of 194 amino acids. The 130-nucleotide long 3' untranslated region contains the putative polyadenylation signal 30 bases upstream from the 3' end of the RNA.

Comparison of the amino acid sequence of TIMP-2 deduced from the cDNA clone with that determined by direct amino acid sequencing of overlapping endoproteinase derived peptide fragments shows excellent agreement. The original sequence contained only 192 amino acids. The previously unidentified residues correspond to the glycyl residue at positions 92 and the prolyl residue at the carboxyl terminus. Other changes are noted in FIG. 8. The homology of TIMP-2 with TIMP-2 at the predicted amin acid sequence level is 37.6% identity and 65.6% overall homology. Pustell Matrix analysis of the homology distribution between these two predicted protein sequences using a cutoff value of 66% and an 8 amino acid overlap, demonstrates that there are two areas in which the homology falls below this average value. TIMP-2 shows a distinct preference for binding to the latent form of the 72 kDa type IV collagenase in the presence of both other latent metalloproteinases and TIMP-1 (Stetler-Stevenson et al., 1989, *J. Biol. Chem.* 264, 17374–17378; Goldberg et al., 1989, *Proc. Natl. Acad. Sci. USA* 86, 8207–8211). However, both forms of TIMP will inhibit activated type IV collagenase. Thus regions of amino acid sequence that are highly conserved between these proteins, such as those that exceed the overall homology value of 66%, may be responsible for the known shared functions of these proteins, inhibition of the activated collagenase family enzymes which are unique for individual TIMP molecules. Thus, the regions of low homology between residue 20 to 45 and the carboxyl terminus of TIMP-2, may be responsible for the binding of TIMP-2 to the latent form of the 72 kDa type IV collagenase.

EXAMPLE 5

Applications of the TIMP-2 cDNA.

Figure 9:
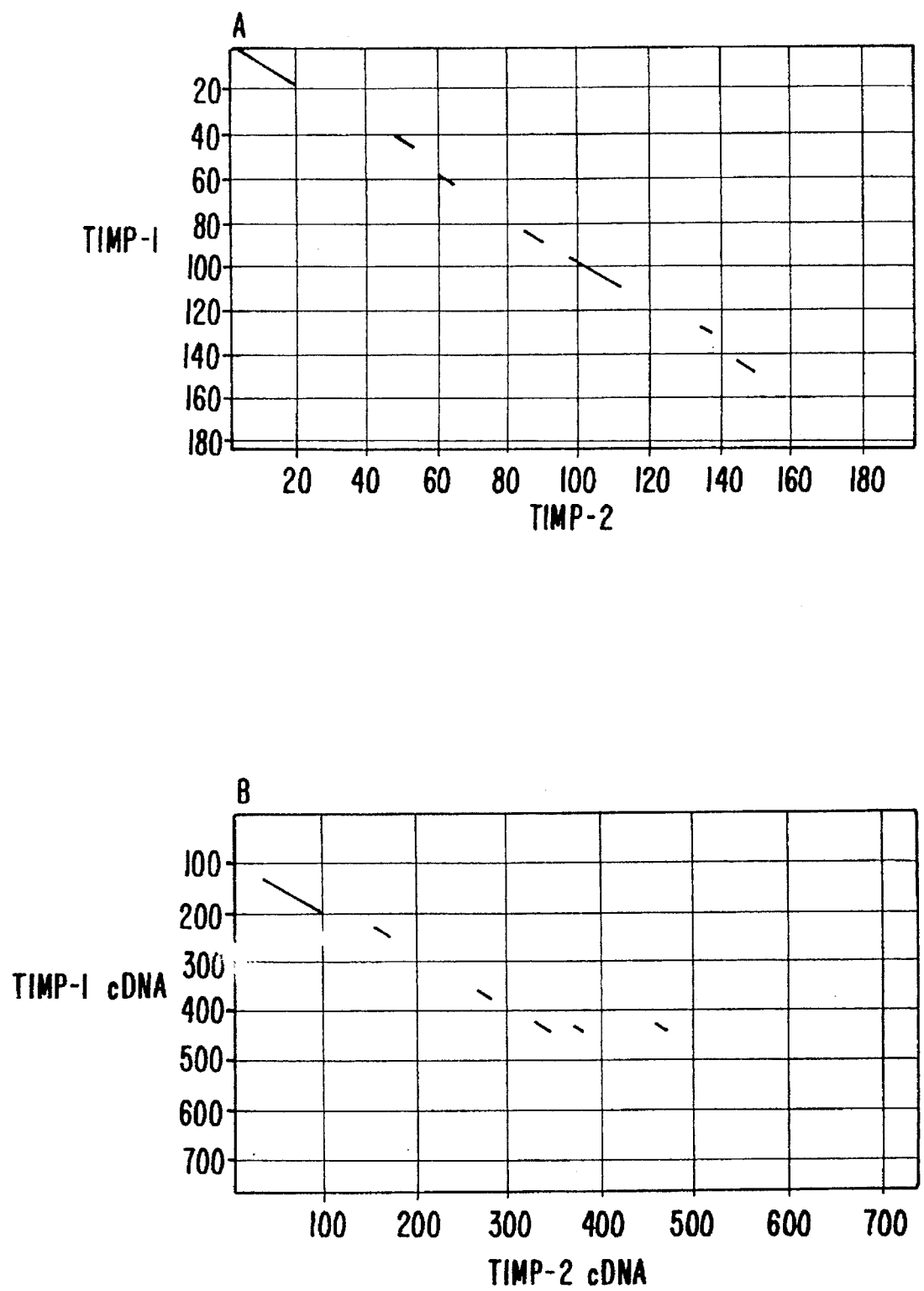
FIG. 9. Homology comparison of TIMP-2 and TIMP-1 at the amino acid (A) and nucleotide levels (B). A. Deduced amino acid sequences of TIMP-2 and TIMP-1 were compared using a Pustell Scoring Matrix. The analysis was performed using a cutoff value of 66% homology, and an 8 amino acid overlap. The line denotes regions in which the homology exceeds the average value of 66% homology between these two protein. B. Comparison of the nucleotide sequences of TIMP-2 and TIMP-1. Analysis was performed using a Pustell Scoring Matrix, with a hash value of 4 and a window of 30. The line indicates regions of identity. The analysis if performed for TIMP-1 vs. TIMP-1 or TIMP-2 vs. TIMP-2 gives a solid line on the diagonal, indicating complete identity. This demonstrates that TIMP-2 is a unique gene product distinct from TIMP-1.

Comparison of the cDNA sequence of human TIMP-2 with that of human TIMP-1 shows little homology compared to that seen at the amino acid level, FIG. 9b. This result implies that these genes diverged early in the evolution of this gene family. The lack of homology at the cDNA level may also explain why TIMP-2 mRNA transcripts are not detected in northern blot analyses using TIMP1 probes and also why screening cDNA libraries with TIMP-1 probes fails to yield TIMP-2 clones.

Northern blot analysis of oligo-dT selected mRNA isolated from various cells have been carried out using the TIMP-2 cDNA. HT-1080 human fibrosarcoma cells, WI-38 human embryonic lung fibroblasts, and A2058 human melanoma cells were grown to 80% confluence in Dulbecco's modified Eagle medium (DMEM, GIBCO). The medium was then replaced with DMEM supplemented with 0.5% ITS$^+$ (Collaborative Research Inc.) and 25 µg/mL Gentamycin. The medium was changed after 4 hours and culture continued for 20 hours prior to the addition of 10 ng/mL TPA (Sigma Chemical Co.) or 5 ng/mL TGF-Dβ1 (R & D Systems).

Total cytoplasmic RNA was isolated from cell lines as described (Gough 1988, *Anal. Biochem.* 173, 93–95). mRNA was isolated using the FAST-TRACK mRNA isolation kit (Invitrogen). Tissues mRNA was isolated from frozen tissue fragments. Tissue fragments were obtained from three partial colectomy specimens at the time of surgery, from Dr. Barry Schmuckler, Washington Hospital Center, Washington, D.C. The pathologic diagnosis of all three cases was invasive adenocarcinoma. Tissue samples were also obtained from adjacent, uninvolved mucosa. Frozen tissue was pulverized in liquid $N_2$ using a mortar and pestle. The tissue powder was then dissolved in 4 M guanidine isothiocyanate, 3 M sodium acetate, 0.84% β-mercaptoethanol, pH 6.0. Total cytoplasmic RNA was isolated by pelleting through 5.7 M cesium chloride, 3 M sodium acetate, pH 6.0. Aliquots of RNA were applied to formaldehyde/1% w/v agarose gels and electrophoresed before transfer onto Nytran filters (Schleicher & Schuell). The RNA was UV-crosslinked to the filter and hybridized to the insert from clone pSS38. The pSS38 cDNA probe was labelled with α-[$^{32}$P]-dCTP using a random primer labelling kit (Bethesda Research Laboratories).

Figure 10:
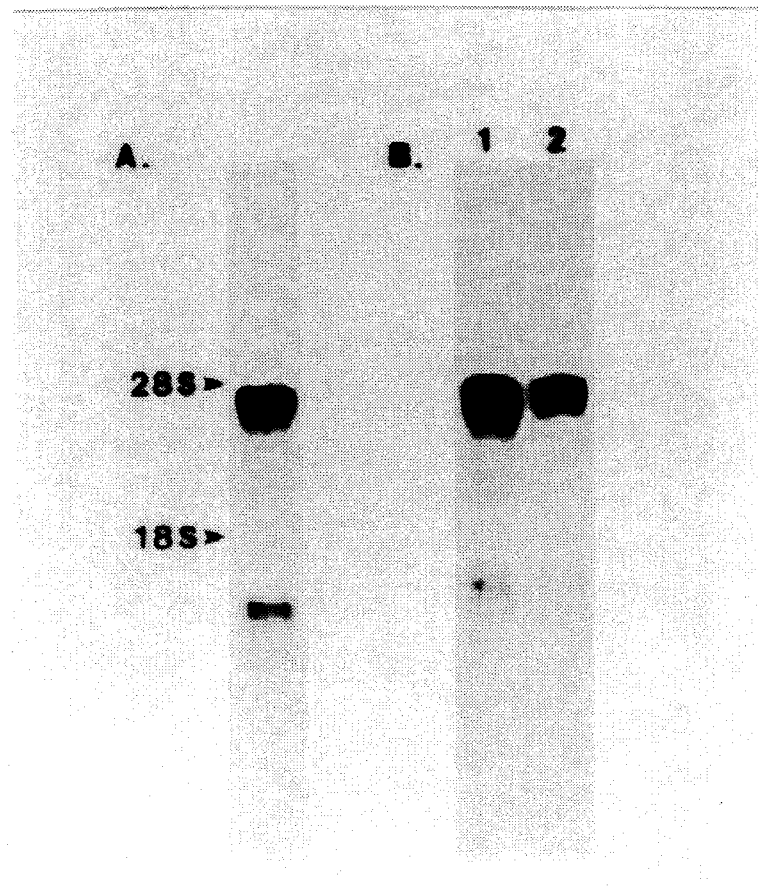
FIG. 10. Northern blot analysis of TIMP-2 mRNA expression in cultured cell lines. Total cytoplasmic and oligo-dT selected RNA as isolated from cells as described in the text. After transfer to Nytran filter RNA was hybridized with $^{32}$P-labelled probe specific for TIMP-2. The resulting autoradiographs and shown. A). Oligo-dT selected RNA (1µg) from A2058 human melanoma cells. B) . Total cytoplasmic RNA (5µg) from WI-38 human embryonic fibroblasts (lane 1) and HT-1080 human fibrosarcoma cells (lane 2).

Northern blot analysis of the A2058 human melanoma cell line revealed two specific mRNA species with approximate sizes of 3.5 and 0.9 kb (FIG. 10a). These mRNA species were also detected in RNA isolated from human WI-38 fibroblasts, with very low levels of the 0.9 kb species detectable in equivalent amounts of RNA from HT-1080 fibrosarcoma cells (FIG. 10b). The origin of these two specific transcripts remains to be determined, however the size difference is too large to be easily accounted for by differences in 3', polyadenylation. It is possible that alternative 5' untranslated regions could account for the different transcript sizes, as has been demonstrated for insulin-like growth factor II mRNA's.

Figure 11:
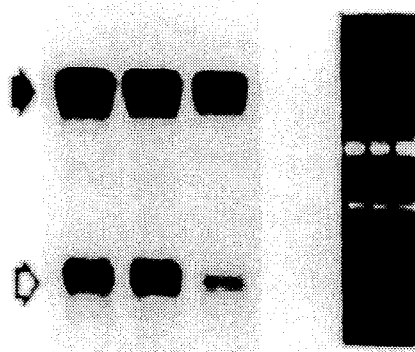
FIG. 11. Northern blot analysis of total cytoplasmic RNA isolated from A2058 melanoma cells following 48 hour treatment with either 12-tetradecanoylphorbol 13-acetate (10 ng/mL, lane B) or transforming growth factor β1 (5ng/mL, lane C). These are compared with basal levels in untreated A2058 cells (lane A). Equal amounts of RNA (5 µg) were loaded and the ethidium bromide stained gel is shown as a control (insert).

Treatment of A2058 cells with 12-0tetradecanoylphorbol 13-acetate (TPA) (10 ng/ml) for 48 hours failed to significantly modulate TIMP-2 transcript levels (FIG. 11). This is in contrast to mRNA level for the 72 kDa type IV collagenase, which was down regulated in response to TPA. Interstitial collagenase mRNA is rapidly induced following TPA treatment of A2058 melanoma cells and fibroblast cells lines (Chin et al., 1985, *J. Biol. Chem.* 260, 12367–12376; Werb et al., 1986, *J. Cell Biol.* 102, 697–702; Frisch et al., 1987, *Proc. Natl. Acad. Sci. USA* 84, 2600–2604), as is TIMP-1 (Edwards et al., 1985, *Mol. Cell. Biol.* 5, 3280–3288; Murphy et al., 1985, *J. Biol. Chem.* 260, 3079–3083; Welgus et al., 1985b, *J. Clin. Invest.* 76, 219–224). Treatment of A2058 melanoma cells with transforming growth factor-beta 1 (TGF-β1) for 48 hours resulted in a clearly detectable decrease in TIMP-2 mRNA levels (FIG. 11). The 3.5 and 0.9 kb transcripts showed equal decreases in steady-state level, and there was no indication of differential expression. TGF-β1 has been demonstrated to increase TIMP-1 mRNA levels in human gingival fibroblasts (Overall et al., 1989, *J. Biol. Chem.* 264, 1860–1869). It has been demonstrated previously that TGF-β1 induced the 72 kDa type IV collagenase mRNA and protein levels, as well as enzyme activation. In the presence of the other growth factors, TGF-β1 also has a selective reciprocal effect on interstitial collagenase and TIMP-1 expression (Edwards et al., 1987, *EMBO J.*, 1899–1904). TGF-β1 selectively represses the induction of interstitial collagenase, but interacts synergistically to super-induce TIMP-1. These data demonstrate that TIMP-1 and TIMP-2 respond differently to TPA treatment and oppositely to TGF-β1 treatment. Furthermore, TGF-β1 has a reciprocal effect on TIMP-2 and the 72 kDa type IV collagenase transcript levels in human melanoma cells. Thus it is clear that the transcriptional regulation of TIMP-2 is independent of TIMP-1.

Finally, northern blot analysis of tissue from three primary, human colorectal tumors and adjacent normal mucosa was performed using the pSS38 TIMP-2 probe and is presented in FIG. 12. The matched samples showed no detectable change in TIMP-2 mRNA transcript levels between the colorectal tumor samples and the adjacent normal mucosa. Previous studies have shown that indeed human colorectal tumor tissue contains elevated type IV collagenase mRNA transcripts. These data suggest that in the primary tumor cell population the ratio of TIMP-2 to 72 kDa type IV collagenase is altered in favor of the enzyme species by differential transcription. However, due to primary tumor cell heterogeneity and the possible inclusion of normal cell populations in the invasive tumor samples, this observation may not accurately reflect the invasive, metastatic cell subpopulations. Examination of metastatic lesions will allow a better understanding of the role of these proteins in tumor cell invasion.

Utility of the CSC-21K cDNA Clones

The isolated human cDNA clones encoding the metalloproteinase inhibitor protein, TIMP-2, have wide utility in diagnostics. Pathologic conditions including neoplasia, inflammatory diseases, cardiovascular disease, central nervous system disorders, diabetes and abnormalities of growth and development may be accompanied or causally related to abnormal levels of metalloproteinase inhibitor protein, the subject of invention. All of these processes may involve abnormal accumulation or loss of extracellular matrix proteins. In particular, many of these disease states exhibit abnormal basement membranes. Since control of basement membrane breakdown may be regulated by inhibitors of metalloproteinase action, the inhibitor protein of the subject invention may play a key role in determining the steady-state levels of basement membranes. The present cDNA clones encoding the inhibitor protein CSC-21K can be used in northern blotting analysis to measure the mRNA levels of the inhibitor in RNA samples isolated from tissue samples or cultured cells, as described in Example 5 (above). In some cases, elevated CSC-21K mRNA levels detected in this fashion may reflect pathologic states leading to increased basement membrane accumulation, such as diabetes mellitus. In other cases, loss of the inhibitor protein may be important, such as in neoplasia and central nervous system disorders involving the basement membrane surrounding nerves. In addition to hybridization of the isolated cDNA clone (whole or in part) with isolated RNA or DNA, in situ hybridization using tissue or cell samples can be readily conducted using methods well known in the art. For this and other purposes, the clone can be labeled with radioactive markers for detection by using suitable enzymes and radioactive precursors.

The inhibitor protein CSC-21K is a suppressor of neoplastic invasion, and as such, is a tumor suppressor gene. Therefore, homozygous loss, allelic loss, or mutational inactivation of the gene regulatory region may suppress expression of the inhibitor and favor the development of cancer. All of these genetic defects can be detected using the isolated cDNA clone in standard Southern blotting analysis, with or without prior polymerase chain reaction amplification of sample DNA sequences, with methods and appropriate restriction enzymes well known in the art. Extraction of DNA and measurement of such genetic defects may be useful in the diagnosis of cancer and the detection of individuals with hereditary defects predisposing to the development of cancer.

The isolated cDNA clones may be useful in genetic therapy. Diseases associated with loss or down regulation of expression of the subject inhibitor protein could be treated with the cDNA clone in a suitable expression vector, allowing augmented synthesis of the CSC-21K protein. Transfection of the cDNA clone for CSC-21K, in an expression vector with a suitable promoter, into a cell deficient in CSC-21K production would result in the increased production of CSC-21K and correction of the abnormal phenotype. Alternatively, antisense constructs, using the same expression vector but containing the reverse orientation of the CSC-21K cDNA insert, could be used to suppress the overproduction of metalloproteinase inhibitor protein. This could be useful in disorders of abnormal regulation or inappropriately high production of the CSC-21K inhibitor protein. The system and methods of preparation of such genetic reagents is known in the art, but requires the specific isolated nucleotide sequence of the invention. It is obvious that the cDNA clone of the present invention could be spliced next to a gene encoding any other protein to produce a hybrid protein. This methodology could be used to produce a hybrid protein with enhanced inhibitory activity or tumor-seeking behavior.

The cDNA clone, or any other DNA segment of this invention which encodes the amino acid sequence of the TIMP-2 protein (according to the universal genetic code) is necessary and highly useful for the recombinant production of inhibitor protein CSC-21K (TIMP-2). Recombinant CSC-21K can be made in any suitable expression system, either prokaryotic or eukaryotic. A significant advantage in the production of the present invention is that the protein is not glycosylated, and does not require post-translational modification for functional activity. Thus, recombinant proteins made in bacterial expression systems can be functionally active directly as obtained from the culture medium. It is obvious that the recombinant inhibitor protein can be linked to suitable carrier proteins, marker proteins or other compounds which stabilize or potentiate its activity. The recombinant protein whole, or in part, can be used as an antigen or treatment agent to inhibit metalloproteinase action.

The cDNA clone of the subject invention encodes a novel metalloproteinase inhibitor CSC21K. The gene itself is novel and distinct encodes a novel metalloproteinase inhibitor CSC21K. The gene itself is novel and distinct from all prior art reporting cDNA clones encoding proteinase inhibitors. In fact, hybridization of any or all of the cDNA clones for proteinase inhibitors existing in the prior art, under either stringent conditions or conditions of reduced stringency, fails to detect the gene of the present invention, whole or in part. For that reason, the gene of the present invention has never before been detected. The affinity purification of this protein, and the identification of the novel amino acid sequence of this invention was a totally original approach, not described in the prior art which led to the isolation of the gene of the present invention.

It is well known in the field of protein chemistry that the functional properties of a protein do not depend on the identity of 100% of the amino acid residues which comprise the protein. Individual amino acid residues can be substituted which have the same charge or hydrophobicity and achieve the same function. Furthermore, other amino acids in a protein molecule which specifically function to determine the protein structure can substituted with residues which differ in charge or hydrophobicity without diminishing the overall biological activity of the parent protein molecule. More generally, the degree of evolutionary similarity of the amino acid sequences of two structurally and functionally related polypeptides is determined by the method of quantitative analysis defined by the sequence alignment and comparison algorithms described by Pearson and Lipman (Pearson, W. R. & Lipman, D. J., 1988, *Proc. Nat. Acad. Sci. U.S. A.* 85:2444–48). This quantitative comparison contemplates not only precise homology of amino acid sequences, but also substitutions of one residue for another which are known to occur frequently in families of evolutionarily related proteins sharing a conserved function. Thus, in the present case, this invention also relates to an isolated polypeptide which inhibits a matrix metalloproteinase and which has an amino acid sequence that differs in at least one position from the sequence defined in FIG. 7 and yet has greater similarity to the amino acid sequence of FIG. 7, or to a unique portion thereof, than to the amino acid sequence of any other polypeptide.

When matrix metalloproteinase inhibitors of the invention are used in the treatment of inappropriate angiogenesis, arthritis, tumor growth, invasion and metastasis, and granu-lomatous inflammatory conditions such as sarcoidosis and other pathological conditions, it is possible to estimate the amount of enzyme produced and the amount of peptide inhibitor required to inhibit greater than 90% of the active enzyme. For use in treating any disease condition, the therapeutic dose of the inhibitory peptide falls within an acceptable pharmacologic range of 1-250 mg/kg/da, with a more preferred dosage being 25-100 mg/kg/d. The dosage for a given patient will depend on the amount of enzyme produced in the patient, the condition and size of the patient. The inhibitors may be given as infusions or by any means which provides ready transmission into the circulation. Lyophilized powders may be "snorted". Preparations for buccal or sublingual administration may also be given. For respiratory tract involvement, the peptides may be administered by inhalation. Aerosols are particularly useful for this purpose. For conditions of the eye, the peptides may be administered as eye drops.

The isolated CSC-21 proteins, natural or recombinant, or active peptides derived therefrom can be administered intravenously, orally, intrauterine, by inhalation or topical application. For example, topical application can be prepared using a suitable carrier for treatment of basal cell carcinomas or melanomas of the skin or for the treatment of corneal ulceration.

The complete CSC-21 protein or CSC-21 peptides can be produced by purification from natural sources, by synthetic peptide chemistry methods or by recombinant DNA technology. In the latter case, suitable cDNA clones for CSC-21 in a suitable expression vector can be used to produce peptides with CSC-21 activity.

CSC-21 peptides and antibodies to CSC-21 are also useful in diagnosis of diseases characterized by abnormal balances of matrix metalloproteinase and associated inhibitor. Purified CSC-21 may be used by virtue of its ability to bind metalloproteinases as a means to purify and or detect metalloproteinases from any natural source. Suitable immunoassays for CSC-21 could include anti-CSC-21 antibodies, reference CSC-21 antigen and solid or solution phase reactions. Purified CSC-21 or peptide domains of CSC-21 can be tagged with suitable enzymatic, fluorescent or radioactive labels by means well known in the art.

Peptides lacking a cysteine or having only one cysteine were found to be useful in assays to detect metalloproteinase and as means of purifying metalloproteinases and are also a part of the invention. Three such structures were peptides having the amino acid sequences:

DIYGNPIKRIQYEIK-QIKKFKGIEKDIEFIYTAPSSAVCGVELDVGGK, DVGGKKEYLIAGKAEDGKRHITL, and RHITLCD-FIVPWDTLSTTQKKSLN.

Peptides of the invention may be used in tests to assay metalloproteinases in animal or human tissues or in body fluids which may have antibodies to the protein. Peptides may also be used to elicit antibodies for use in detecting metalloproteinases.

The amino acids herein are given the usual one letter abbreviations accepted as:

| | |
|---|---|
| A is Alanine | C is Cysteine |
| D is Aspartic Acid | E is Glutamic Acid |
| F is Phenylalanine | H is Histidine |
| I is Isoleucine | K is Lysine |
| L is Leucine | M is Methionine |
| N is Asparagine | P is Proline |

-continued

| | |
|---|---|
| Q is Glutamine | R is Arginine |
| S is Serine | T is Threonine |
| V is Valine | W is Tryptophan |
| X is Tyrosine | Y is Pyroglutamic Acid |

For purposes of completing the background description and present disclosure, each of the published articles, patents and patent applications heretofore identified in this specification are hereby incorporated by reference into the specification.

What is claimed is:

1. An isolated nucleic acid having a sequence which encodes the 194 amino acid polypeptide of FIG. 8.

2. An isolated nucleic acid of claim 1 having a sequence of FIG. 7.

3. An isolated nucleic acid of claim 1, wherein a promoter is operably linked to the nucleic acid.

4. An isolated nucleic acid of claim 3, wherein the promoter and the nucleic acid are contained in an expression vector.

5. A cell transformed or transfected with a nucleic acid of claim 1.

6. A cell transformed or transfected with a nucleic acid of claim 4.

7. A method of producing the 194 amino acid polypeptide of FIG. 8 by introducing into a suitable host cell an expression vector having a promoter operably linked to a nucleic acid which encodes said polypeptide and recovering said polypeptide from said cell.

* * * * *